United States Patent [19]

Tilles et al.

[11] 4,147,715
[45] Apr. 3, 1979

[54] THIOCARBAMATE PREPARATION UTILIZING QUATERNARY AMMONIUM SALT CATALYSTS

[75] Inventors: Harry Tilles, El Cerrito; Paul E. Hoch, Moraga, both of Calif.

[73] Assignee: Stauffer Chemical Company, Westport, Conn.

[21] Appl. No.: 889,175

[22] Filed: Mar. 23, 1978

[51] Int. Cl.$^2$ .................. C07C 153/09; C07D 207/24; C07D 211/06; C07C 87/30

[52] U.S. Cl. .................. 260/455 A; 260/326.4; 260/239 E; 260/239 A; 260/239 B; 260/567.6 R; 546/226; 546/245; 546/314; 546/328

[58] Field of Search .......... 260/455 A, 326.4, 293.85, 260/239 E, 239 A, 239 B, 567.6 R, 239 AR, 239 AL

[56] References Cited

U.S. PATENT DOCUMENTS

| | | | |
|---|---|---|---|
| 3,167,571 | 1/1965 | D'Amico et al. | 260/455 A |
| 3,330,643 | 7/1967 | Harman et al. | 71/88 |
| 3,992,432 | 11/1976 | Napier et al. | 260/465.1 |

*Primary Examiner*—Elbert L. Roberts
*Assistant Examiner*—Robert C. Whittenbaugh
*Attorney, Agent, or Firm*—M. Henry Heines

[57] ABSTRACT

Thiocarbamates are prepared by a process comprising reacting an aqueous solution of a thiocarbamate salt with an organic halide in the presence of a catalytic amount of a quaternary ammonium salt having the formula $$(R^4R^5R^6R^7N)^+Y^-$$

in which $R^4$ and $R^5$ are independently selected from the group consisting of $C_1$–$C_{25}$ alkyl and $C_2$–$C_{25}$ alkenyl, $R^6$ and $R^7$ are independently selected from the group consisting of $C_6$–$C_{25}$ alkyl and $C_6$–$C_{25}$ alkenyl, and $Y^-$ is an anion selected from the group consisting of chloride and bromide; and separating the thiocarbamate from the aqueous solution.

12 Claims, No Drawings

THIOCARBAMATE PREPARATION UTILIZING QUATERNARY AMMONIUM SALT CATALYSTS

BACKGROUND OF THE INVENTION

The esters of thiocarbamic acids, referred to herein as "thiocarbamates," are well known in the art of agricultural chemicals for their utility and commercial value. Some thiocarbamates are active herbicides, others are effective for inhibiting the growth of microorganisms such as bacteria, and still others are active insecticides. Thiocarbamates are also widely used in combination with other active compounds for synergistic effect, and in numerous formulations applicable to a wide variety of uses.

Thiocarbamates have the general formula

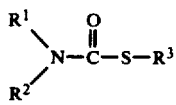

in which the R-groups can represent a wide variety of organic radicals. Compounds of this molecular configuration are alternately referred to in the chemical literature as "thiolcarbamates," the terms being used interchangeably to designate the same type of compound.

The object of this invention is to provide a novel process for the manufacture of thiocarbamates, one which will provide an improvement in overall yield and process economy. Other objects and advantages will be evident from the discussion which follows.

SUMMARY AND BRIEF DESCRIPTION OF THE INVENTION

This invention provides a novel process for the preparation of members of a class of compounds known as thiocarbamates. More specifically, this invention relates to the discovery that the manufacture of thiocarbamates can be significantly enhanced by the use of certain quaternary ammonium salts as phase transfer catalysts, while other quaternary ammonium salts provide no improvement at all.

In particular, this invention relates to a process for the preparation of thiocarbamates of the formula

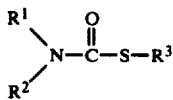

in which $R^1$ and $R^2$ are independently selected from the group consisting of the following substituted or unsubstituted groups: $C_1-C_{12}$ alkyl, $C_2-C_8$ alkenyl, $C_3-C_6$ alkynyl, phenyl, $C_7-C_{10}$ phenylalkyl, $C_3-C_7$ cycloalkyl, $C_5-C_7$ cycloalkenyl, $C_2-C_8$ alkoxyalkyl, $C_2-C_8$ alkylthioalkyl, $C_3-C_8$ alkoxyalkenyl, and $C_3-C_8$ alkylthioalkenyl; wherein the substituents are independently selected from the group consisting of halo, cyano, nitro, trifluoromethyl, $C_1-C_4$ alkyl, and $C_1-C_4$ alkoxy, or $R^1$ and $R^2$ together with the nitrogen atom to which they are bound form a member selected from the group consisting of pyrryl, pyridyl, and $C_2-C_6$ polyalkyleneimine; and $R^3$ is selected from the group consisting of the following substituted or unsubstituted groups: $C_1-C_{12}$ alkyl, $C_2-C_8$ alkenyl, $C_3-C_6$ alkynyl, phenyl, $C_7-C_{10}$ phenylalkyl, $C_3-C_7$ cycloalkyl, $C_5-C_7$ cycloalkenyl, $C_2-C_8$ alkylthioalkyl, $C_3-C_8$ alkoxyalkenyl, and $C_3-C_8$ alkylthioalkenyl; wherein the substituents are independently selected from the group consisting of halo, cyano, nitro, trifluoromethyl, $C_1-C_4$ alkyl, and $C_1-C_4$ alkoxy;

which comprises;

(a) reacting an aqueous solution of a thiocarbamate salt of the formula

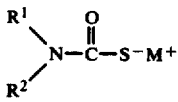

in which $R^1$ and $R^2$ are as defined above and $M^+$ is a cation selected from the group consisting of an alkali or alkaline earth metal ion, the ion $R^1R^2NH_2^+$, and a trialkylammonium ion in which the alkyl groups each contain 1–4 carbon atoms, with an organic halide of the formula

$R^3X$ in which $R^3$ is as defined above and X is chlorine or bromine, in the presence of a catalytic amount of a quaternary ammonium salt having the formula

$(R^4R^5R^6R^7N)^+Y^-$ in which $R^4$ and $R^5$ are independently selected from the group consisting of $C_1-C_{25}$ alkyl and $C_2-C_{25}$ alkenyl, $R^6$ and $R^7$ are independently selected from the group consisting of $C_6-C_{25}$ alkyl and $C_6-C_{25}$ alkenyl, and $Y^-$ is an anion selected from the group consisting of chloride and bromide; and (b) separating said thiocarbamate from said aqueous solution.

Within the scope of the invention, certain embodiments are preferred:

In one such embodiment, $R^1$, $R^2$, and $R^3$ are independently selected from the group consisting of $C_1-C_{12}$ alkyl and $C_2-C_8$ alkenyl, each optionally substituted with one, two, or three halogen atoms, and $M^+$ is an alkali or alkaline earth metal cation.

In another such embodiment, $R^1$ and $R^2$ are independently $C_1-C_{12}$ alkyl, and $R^3$ is $C_2-C_8$ alkenyl optionally substituted with one, two, or three halogen atoms, and $M^+$ is a sodium or potassium ion.

In a further preferred embodiment, $R^4$ is methyl; $R^5$ is selected from the group consisting of methyl, $C_6-C_{20}$ alkyl, and $C_6-C_{20}$ alkenyl; and $R^6$ and $R^7$ are independently selected from the group consisting of $C_6-C_{20}$ alkyl and $C_6-C_{20}$ alkenyl.

In a still further preferred embodiment, $R^4$ is methyl; $R^5$, $R^6$, and $R^7$ are independently $C_6-C_{12}$ alkyl; and $Y^-$ is chloride.

Further preferred embodiments will be evident from the following description.

DETAILED DESCRIPTION OF THE INVENTION

The process of the present invention is most conveniently executed by adding the organic halide to an aqueous solution of the thiocarbamate salt. The catalyst may be already present in the reaction mixture, or it may be added concurrently with the addition of the organic halide, or soon thereafter. This reaction is exothermic. Thus, depending on the quantity of each reactant used, its concentration in the reaction mixture, and its particular enthalpy, it may be necessary to avoid sharp temperature rises by performing the halide addition slowly.

While there is no critical temperature range for this reaction, temperature control is often desirable since the thiocarbamate salt tends to decompose at a rate which increases with increasing temperature. The operating temperature range will thus be dictated by considerations of process economy, such as desired purity, permissible reaction times, and the cost of external cooling and product recovery. In terms of operational economy, it will be most convenient to run the reaction at a temperature between about 0° C. and about 30° C. Temperature control can be achieved by external cooling supplied by any conventional means known in the art, including coils, jackets, and the like.

Stability of the thiocarbamate salt is further enhanced when the latter is in aqueous solution. The use of an aqueous solution is convenient in this process, particularly when the thiocarbamate salt itself is generated in such solution, by reaction between an amine, carbonyl sulfide, and a base, as more fully described hereinbelow.

While the reaction will proceed with undissolved salt, it is generally preferred to have the salt fully dissolved in the aqueous phase for ease of handling and improved reactant contact. Since the organic halide is generally insoluble or only partially soluble in the aqueous phase, the reaction mixture comprises two liquid phases, with a single reactant located in each phase. For this reason, the progress of the reaction can be significantly enhanced by external agitation. While the reaction will proceed without such agitation, it is preferred that some kind of agitation be utilized both to enhance the reaction rate, and to provide a more uniform temperature, preventing the formation of hot spots in the reaction mixture. Agitation can be supplied by any conventional means, including stirrers, baffle plates in the reaction vessel, turbulence columns and the like.

The organic phase may consist either of the organic halide itself or the latter dissolved in a non-reactive solvent. Conventional aliphatic, aromatic, and ether solvents, or chlorinated derivatives thereof, are suitable for this purpose. Solvents which are unsuitable for use in this process due to their reactivity with carbonyl sulfide include alcohols, amines, and mercaptans.

The thiocarbamate salts for use in the present reaction can be prepared by any technique known in the thiocarbamate art. As indicated above, a convenient method for preparation is that by which the appropriate secondary amine ($R^1R^2NH$) is reacted, with carbonyl sulfide and an appropriate base. The base used will be determined by the thiocarbamate salt desired for the final reaction. Thus, the base will either be an alkali or alkaline earth metal hydroxide, a trialkyl amine in which the alkyl groups each contain 1–4 carbon atoms, or the same amine used to form the salt anion, $R^1R^2NH$. Accordingly, an aqueous solution of the amine and the base is prepared, to which gaseous carbonyl sulfide is added.

The carbonyl sulfide is preferably added below the liquid surface and bubbled through the solution. The reaction rate for this reaction is very rapid, producing essentially instantaneous conversion of the reactants to the corresponding thiocarbamate salt. Like the salt/halide reaction, the amine/COS/base reaction is also exothermic, and salt decomposition is again a problem. In fact, the problem may be of greater concern in this reaction since a high concentration of thiocarbamate salt is present for a longer period of time. It is thus desirable to maintain a low temperature by external cooling to suppress the decomposition as much as possible. In addition to the cooling methods described above, the reaction temperature can also be controlled by the rate of addition of carbonyl sulfide. While there is no critical operating range, it will be most convenient to run the reaction at a temperature of about 0° C. to about 30° C., preferably from about 0° C. to about 15° C.

For maximum amine efficiency, the reaction is preferably run using excesses of both carbonyl sulfide and the base. While the amount of excess is purely a question of process economy, such as raw material costs and recovery expenses, the reaction is most conveniently run at a carbonyl sulfide excess of up to about 100% and an excess of base of up to about 20%.

The present invention can be practiced in batch-wise or continuous form, or a combination of the two. When the invention is practiced in batch-wise manner, the chemical species will be combined in a pre-determined series of steps into a single body of liquid. When a continuous form is used, the desired reaction rate can be achieved by selecting a suitable type of agitation, rate of addition, feed point placement, and appropriate reaction conditions. The choice between the various types of process to be used will depend on the desired manufacturing conditions. The reaction vessel or vessels will preferably consist of non-corrosive materials, such as mild steel, which will not interfere with the principal reaction.

Upon completion of the process reaction, the product thiocarbamate will remain in the organic phase. Salt which may have precipitated during the reaction can be dissolved readily by the addition of water. The two liquid phases are subsequently separated. The organic phase, consisting primarily of the thiocarbamate, can be formulated for use without further purification. Alternatively, the organic phase can be dried and the product can be recovered therefrom by purging with argon or nitrogen or applying a vacuum while heating to remove volatiles. Further purification can be achieved by conventional purification techniques.

As used in this specification:

"alkyl" refers to a monovalent straight or branched chain saturated aliphatic hydrocarbon group, for example methyl, ethyl, propyl, i-propyl, t-butyl, or 2-methyl octyl;

"alkenyl" refers to a monovalent straight or branched chain aliphatic hydrocarbon group containing at least one double bond, for example allyl, butenyl, or butadienyl;

"alkynyl" refers to a monovalent straight or branched chain aliphatic hydrocarbon group containing at least one triple bond, for example propargyl or isobutynyl;

"phenylalkyl" refers to an alkyl group as defined above, in which a hydrogen atom is replaced by a phenyl group, for example benzyl or phenylethyl;

"cycloalkyl" refers to a monovalent cyclical saturated hydrocarbon group, for example cyclobutyl or cyclohexyl;

"cycloalkenyl" refers to a monovalent cyclical hydrocarbon group containing at least one double bond, for example cyclohexenyl;

"alkoxyalkyl" refers to an alkyl group as defined above, in which a hydrogen atom is replaced by a monovalent straight or branched chain saturated aliphatic hydrocarbonoxy group, for example methoxyethyl or ethoxyethyl;

"alkylthioalkyl" refers to an alkyl group as defined above, in which a hydrogen atom is replaced by a monovalent straight or branched chain saturated aliphatic hydrocarbonthio group, for example methylthioethyl or ethylthioethyl;

"alkoxyalkenyl" refers to an alkenyl group as defined above, in which a hydrogen atom is replaced by a monovalent straight or branched chain saturated aliphatic hydrocarbonoxy group, for example ethoxybutenyl;

"alkylthioalkenyl" refers to an alkenyl group as defined above, in which a hydrogen atom is replaced by a monovalent straight or branched chain saturated aliphatic hydrocarbonthio group, for example ethylthiobutenyl;

"halo" refers to chloro, fluoro, or bromo; and

"polyalkyleneimine" refers to a monovalent saturated heterocyclic ring in which one member of said ring is a nitrogen atom and the rest are carbon atoms, said ring having the general formula

where n represents the number of carbon atoms indicated where this term is used, for example the groups aziridinyl (n=2), pyrrolydyl (n=4), or piperidyl (n=5).

All carbon atoms ranges stated herein are intended to be inclusive of their upper and lower limits.

The terms "alkali metal" and "alkaline earth metal" refer to elements in Groups IA and IIA, respectively, of the Periodic Chart of the Elements (*Lange's Handbook of Chemistry*, Revised Tenth Edition, McGraw-Hill, 1967). The alkali metals are preferred over the alkaline earth metals, and sodium and potassium, particularly sodium, are the most preferred among the alkali metals.

Examples of thiocarbamic acid esters which can be prepared by the process of the present invention are:
S-ethyl di-n-propylthiocarbamate
S-ethyl hexahydro-1H-azepine-1-carbothioate
S-ethyl diisobutylthiocarbamate
S-n-propyl di-n-propylthiocarbamate
S-ethyl cyclohexyl ethylthiocarbamate
S-n-propyl n-butyl ethylthiocarbamate
S-p-chlorobenzyl diethylthiocarbamate
S-2,3,3-trichloroallyl diisopropylthiocarbamate Examples of quaternary salts which can be used in the process of the invention are tricaprylylmethylammonium chloride (ALIQUAT ® 336) and dimethyldicocoammonium chloride (ALIQUAT ® 221). The latter two catalysts are commercially available products, manufactured by General Mills Co., Chemical Division, Kankakee, Ill. The term "caprylyl" denotes a mixture of straight chain saturated alkyl groups of 8 to 10 carbon atoms, with the 8-carbon chain predominating, while the term "coco" denotes a mixture of straight chain alkyl groups of 8 to 18 carbon atoms, both saturated and unsaturated, with the 12-14 carbon chains predominating.

Mixtures of quaternary salts can also be utilized in the practice of the invention. Double or multi-functional quaternary salts in which the general formula $(R^4R^5R^6R^7N)^+X^-$ is repeated a plurality of times with the same or different substituent combinations, can also be utilized effectively.

The term "catalytic amount" is used herein to represent any amount of quaternary salt which will enhance the progress of the reaction. The amount of quaternary salt normally will range from about 0.2 to about 5.0 weight % of the reaction mixture, preferably from about 0.5 to about 1.0 weight %.

Specific examples are set forth below showing the preparation of thiocarbamates by the process of the present invention. These examples are included for illustrative purposes only, and are not to be interpreted as imposing any limitations on the scope of the invention herein described. Such limitations are set forth in the appended claims.

EXAMPLE 1

This example illustrates three preparations of S-2,3,3-trichloroallyl diisopropylthiocarbamate: the first using no catalyst, the second using tricaprylylmethylammonium chloride (ALIQUAT 336 ®, General Mills Co.) as a catalyst, and the third using a benzyltriethylammonium chloride as a catalyst. Although each of these catalysts are quaternary ammonium salts, only tricaprylylmethylammonium chloride is within the scope of the present invention. The exclusion of benzyltriethylammonium chloride from the present invention is readily discernable from an examination of the $R^4$, $R^5$, $R^6$, and $R^7$ group definitions given above.

Tricaprylylmethylammonium chloride (ALIQUAT 336 ®) is a product of the General Mills Co., Chemical Division, Kankakee, Ill. The term "caprylyl" designates a mixture of straight chain, saturated alkyl groups of 8 to 10 carbon atoms, with the 8-carbon chain predominating.

The procedure followed in each of the three preparations was the same. A mixture of 31.9 grams (g) (0.315 mole) of diisopropylamine, 12 g (0.300 mole) of sodium hydroxide, and 100 cubic centimeters (cc) of water was prepared. The mixture was placed in an ice bath with constant stirring where its temperature was maintained at 2°-6° C. while 20 g (0.330 mole) of carbonyl sulfide was bubbled below the liquid surface. At the completion of the carbonyl sulfide addition, 54.0 g (0.300 mole) of 1,1,2,3,-tetrachloro-1-propene was added rapidly. When a catalyst was used, it was added immediately following the tetrachloropropene addition. When the tricaprylylmethylammonium chloride catalyst was used, the tetrachloropropene was added as a solution in 20 cc of methylene chloride. When the benzyltriethylammonium chloride was used, the tetrachloropropene was added as a solution in 100 cc of benzene. In each case, 0.50 g of catalyst was used.

Following the addition of the tetrachloropropene and the catalyst, the mixture was held in the ice bath for several hours more. Samples of the reaction mixture were analyzed at various intervals by gas chromatography. The results of these analyses are shown in Table 1. An examination of these results shows that tricaprylylmethylammonium chloride (catalyst A) produces a significant increase in the reaction rate over the rate achieved with no catalyst. Benzyltriethylammonium chloride (catalyst B), while showing a slight improvement at the outset, failed to sustain its advantage at 90 minutes of reaction time and thereafter. Conversion actually fell behind that achieved with no catalyst. These results clearly show the unexpected improvement in reaction rate achieved by the use of the process of the present invention.

After the last sample was taken, the reaction flask in each preparation was removed from the ice bath and allowed to come to room temperature with stirring overnight. The two-phase mixture was then diluted with organic solvent and phase separated. The organic phase was then washed with dilute aqueous hydrochloric acid, dried over magnesium sulfate, and concentrated on a rotary evaporator. The molecular structure of the product was confirmed by nuclear magnetic resonance (NMR) and mass spectrometry analyses.

TABLE 1

Preparation of S-2,3,3-Trichloroallyl Diisopropylthiocarbamate

| Reaction Time[a] (Minutes) | Normalized Chromatographic Analysis[b] (Area %) (product/unreacted halide) | | |
|---|---|---|---|
| | No Catalyst | Catalyst A[c] | Catalyst B[d] |
| 15 | 56.1/43.9 | 94.4/5.6 | 63.4/36.6 |
| 90 | 81.2/18.8 | 97.8/2.2 | 70.7/29.3 |
| 240 | 85.1/14.9 | | 72.8/27.2 |

[a]Reaction time is measured from the time of addition of the halide (1,1,2,3-tetrachloro-1-propene)
[b]The results shown are normalized to reflect only the thiocarbamate product and the unreacted halide.
[c]Catalyst A is tricaprylmethylammonium chloride (ALIQUAT 336®)
[d]Catalyst B is benzyltriethylammonium chloride, 97% purity

EXAMPLE 2

This example illustrates two preparations of S-2,3-dichloroallyl diisopropylthiocarbamate: the first using no catalyst, and the second using tricaprylylmethylammonium chloride (ALIQUAT 336®, General Mills Co.) as a catalyst.

The procedure followed in these two preparations was the same as that described in Example 1 above. The results from the gas chromatographic analyses are shown in Table 2. As in Table 1, it is evident upon examination of the figures in Table 2 that a significant enhancement in reaction rate is achieved using a catalyst within the scope of the present invention.

TABLE 2

Preparation of S-2,3-Dichloroallyl Diisopropylthiocarbamate

| Reaction Time[a] (minutes) | Normalized Chromatographic Analysis[b] (Area %) (product/unreacted halide) | |
|---|---|---|
| | No Catalyst | Catalyst A[c] |
| 15 | | 85.4/14.6 |
| 60 | | 92.0/8.0 |
| 98 | 78.0/22.0 | |
| 120 | | 93.3/6.7 |
| 156 | 83.4/16.6 | |

[a]Reactio time is measured from the time of addition of the halide (1,1,2,3-tetrachloro-1-propene)
[b]The results shown are normalized to reflect only the thiocarbamate product and the unreacted halide.
[c]Catalyst A is tricaprylylmethylammonium chloride (ALIQUAT 336®)

What is claimed is:

1. A process for the manufacture of a thiocarbamate of the formula

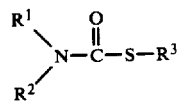

in which
R$^1$ and R$^2$ are independently selected from the group consisting of the following substituted or unsubstituted groups; C$_1$–C$_{12}$ alkyl, C$_2$–C$_8$ alkenyl, C$_3$–C$_6$ alkynyl, phenyl, C$_7$–C$_{10}$ phenylalkyl, C$_3$–C$_7$ cycloalkyl, C$_5$–C$_7$ cycloalkenyl, C$_2$–C$_8$ alkoxyalkyl, C$_2$–C$_8$ alkylthioalkyl, C$_3$–C$_8$ alkoxyalkenyl, and C$_3$–C$_8$ alkylthioalkenyl; wherein the substituents are independently selected from the group consisting of halo, cyano, nitro, trifluoromethyl, C$_1$–C$_4$ alkyl, and C$_1$–C$_4$ alkoxy, or R$^1$ and R$^2$ together with the nitrogen atom to which they are bound form a member selected from the group consisting of pyrryl, pyridyl, and C$_2$–C$_6$ polyalkyleneimine; and R$^3$ is selected from the group consisting of the following substituted or unsubstituted groups: C$_1$–C$_{12}$ alkyl, C$_2$–C$_8$ alkenyl, C$_3$–C$_6$ alkynyl, phenyl, C$_7$–C$_{10}$ phenylalkyl, C$_3$–C$_7$ cycloalkyl, C$_5$–C$_7$ cycloalkenyl, C$_2$–C$_8$ alkoxyalkyl, C$_2$–C$_8$ alkylthioalkyl, C$_3$–C$_8$ alkoxyalkenyl, and C$_3$–C$_8$ alkylthioalkenyl; wherein the substituents are independently selected from the group consisting of halo, cyano, nitro, trifluoromethyl, C$_1$–C$_4$ alkyl, and C$_1$–C$_4$ alkoxy;

which comprises (a) reacting an aqueous solution of a thiocarbamate salt of the formula

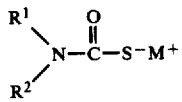

in which R$^1$ and R$^2$ are as defined above and M$^+$ is a cation selected from the group consisting of a alkali or alkaline earth metal ion, the ion R$^1$R$^2$NH$_2^+$, and a trialkylammonium ion in which the alkyl groups each contain 1–4 carbon atoms, with an organic halide of the formula

in which R$^3$ is as defined above and X is chlorine or bromine, in the presence of a catalytic amount of a quaternary ammonium salt having the formula

in which R$^4$ and R$^5$ are independently selected from the group consisting of C$_1$–C$_{25}$ alkyl and C$_2$–C$_{25}$ alkenyl, R$^6$ and R$^7$ are independently selected from the group consisting of C$_6$–C$_{25}$ alkyl and C$_6$–C$_{25}$ alkenyl, and Y$^-$ is an anion selected from the group consisting of chloride and bromide; and (b) separating said thiocarbamate from said aqueous solution.

2. A process according to claim 1 in which M$^+$ is an alkali or alkaline earth metal cation.

3. A process according to claim 1 in which M$^+$ is a sodium or a potassium ion.

4. A process according to claim 1 in which X is chlorine.

5. A process according to claim 1 in which R$^4$ is methyl; R$^5$ is selected from the group consisting of methyl, C$_6$–C$_{20}$ alkyl, and C$_6$–C$_{20}$ alkenyl; and R$^6$ and R$^7$ are independently selected from the group consisting of C$_6$–C$_{20}$ alkyl and C$_6$–C$_{20}$ alkenyl.

6. A process according to claim 1 in which R$^4$ is methyl; R$^5$, R$^6$, and R$^7$ are independently C$_6$–C$_{12}$ alkyl; and Y$^-$ is chloride.

7. A process according to claim 1 in which M$^+$ is a sodium ion; X is chlorine; R$^4$ is methyl, R$^5$, R$^6$, and R$^7$ are independently C$_8$–C$_{20}$ alkyl; and Y$^-$ is chloride.

8. A process according to claim 1 in which $R^1$, $R^2$, and $R^3$ are independently selected from the group consisting of $C_1$–$C_{12}$ alkyl and $C_2$–$C_8$ alkenyl, each optionally substituted with one, two, or three halogen atoms.

9. A process according to claim 1 in which $R^1$ and $R^2$ are independently $C_1$–$C_{12}$ alkyl, and $R^3$ is $C_2$–$C_8$ alkenyl optionally substituted with one, two, or three halogen atoms.

10. A process according to claim 1 in which $R^1$ is isopropyl, $R^2$ is isopropyl, and $R^3$ is 2,3,3-trichloroallyl.

11. A process according to claim 1 in which $R^1$ is isopropyl, $R^2$ is isopropyl, and $R^3$ is 2,3-dichloroallyl.

12. A process according to claim 1 in which the thiocarbamate salt of step (a) is prepared in aqueous solution by reaction between an amine of the formula $R^1R^2NH$, carbonyl sulfide, and a member selected from the group consisting of an alkali or alkaline earth metal hydroxide, a trialkylamine in which the alkyl groups each contain 1–4 carbon atoms, and the amine $R^1R^2NH$, in which $R^1$ and $R^2$ are as defined in claim 1.

* * * * *